US011759539B2

(12) United States Patent
Astl et al.

(10) Patent No.: US 11,759,539 B2
(45) Date of Patent: Sep. 19, 2023

(54) APPARATUS, SYSTEM AND METHOD TO TREAT AIR AND SURFACES USING LIGHT

(71) Applicant: LIND EQUIPMENT LTD., Markham (CA)

(72) Inventors: Brian Astl, Toronto (CA); Sean Van Doorselaer, Toronto (CA)

(73) Assignee: LIND EQUIPMENT LTD., Markham (CA)

(*) Notice: Subject to any disclaimer, the term of this patent is extended or adjusted under 35 U.S.C. 154(b) by 290 days.

(21) Appl. No.: 17/194,961

(22) Filed: Mar. 8, 2021

(65) Prior Publication Data

US 2022/0202979 A1 Jun. 30, 2022

Related U.S. Application Data

(60) Provisional application No. 63/130,493, filed on Dec. 24, 2020.

(51) Int. Cl.
| | | |
|---|---|---|
| *A61L 9/20* | (2006.01) | |
| *B01D 53/00* | (2006.01) | |
| *A61L 2/24* | (2006.01) | |
| *A61L 2/10* | (2006.01) | |

(52) U.S. Cl.
CPC ............... *A61L 9/20* (2013.01); *A61L 2/10* (2013.01); *A61L 2/24* (2013.01); *B01D 53/007* (2013.01); *A61L 2202/11* (2013.01); *A61L 2202/14* (2013.01); *A61L 2209/111* (2013.01); *A61L 2209/12* (2013.01); *B01D 2259/804* (2013.01)

(58) Field of Classification Search
CPC ...... A61L 9/20; A61L 2/10; A61L 2/24; A61L 2202/11; A61L 2202/14; A61L 2209/111; A61L 2209/12; B01D 53/007; B01D 2259/804
See application file for complete search history.

(56) References Cited

U.S. PATENT DOCUMENTS

| | | |
|---|---|---|
| 6,805,733 B2 | 10/2004 | Engel et al. |
| 9,956,306 B2 | 5/2018 | Brais et al. |
| 2003/0170152 A1* | 9/2003 | Kobayashi ............... A61L 9/20 422/186.3 |
| 2017/0299289 A1 | 10/2017 | Brais et al. |
| 2021/0369907 A1* | 12/2021 | Umenei ................ G06F 1/1601 |

FOREIGN PATENT DOCUMENTS

| | | |
|---|---|---|
| CA | 2412673 C | 6/2003 |
| CA | 2991149 C | 1/2017 |

* cited by examiner

*Primary Examiner* — Nicole M Ippolito (57) ABSTRACT

There is provided an apparatus, system and method to treat air and surfaces using light. The apparatus comprises a hollow body having an inlet and outlet for passage of air. Treatment lamps are body mounted for movement between an air treatment position to treat air inside the body and a surface treatment position to treat air/an external surface. When installed in a room environment, the apparatus, via a system controller, operates in an air treatment mode, a surface treatment mode or an off mode. Room sensors (e.g. interlock and presence) communicate with the controller and the controller permits or prevents operation in the surface treatment mode accordingly. If any interlock sensor senses an open position or the presence sensor senses a presence (e.g. motion), operation in the surface mode is prevented. A remote control communicates with the controller to select an operating mode.

20 Claims, 8 Drawing Sheets

APPARATUS, SYSTEM AND METHOD TO TREAT AIR AND SURFACES USING LIGHT

CROSS-REFERENCE

This application claims the benefit of U.S. Provisional Application No. 63/130,493 filed Dec. 24, 2020, which is incorporated herein by reference.

FIELD

This disclosure relates to treating air and surfaces and to an apparatus, system and method to treat air and surfaces using light.

BACKGROUND

Germs such as viruses, bacteria, mold, funghi, and allergens are susceptible to treatment by application of light, particularly Ultraviolet-C (UV-C comprises light at a wavelength between 200-280 nm). A germicidal range may extend beyond UV-C to 300 nm, and include a portion of UV-B spectrum. Treatment via lamps using LED technology, among others, is an effective manner to inactivate such germs.

Excessive human exposure to UV light, including UV-C, is undesirable, for example to skin, eyes, etc.

SUMMARY

There is provided an apparatus, system and method to treat air and surfaces using light as shown and described in embodiments.

In an embodiment, the apparatus comprises a hollow body having an inlet and outlet for passage of air through the body. Treatment lamps are body mounted for movement between an air treatment position facing inwardly of the body to treat air inside the body and a surface treatment position facing outwardly of the body to treat air/an external surface outside the body. When installed in a room environment, in an embodiment, the apparatus, via a system controller (e.g. mounted in the body), operates in an air treatment mode, a surface treatment mode or an off mode. Room sensors (e.g. interlock and presence) communicate with the controller and the controller permits or prevents operation in the surface treatment mode accordingly. If any interlock sensor senses an open position (e.g. of a door or window) or the presence sensor senses a motion or other indication of a presence (e.g. within the room), operation in the surface mode is prevented. A remote control communicates with the controller to select one of the modes.

There is provided an apparatus aspect according to an embodiment where the apparatus comprises: a hollow body having an inlet and an outlet; a fan unit between the inlet and the outlet; and at least one treatment lamp to provide light to effectively inactivate germs, each of the at least one treatment lamp moveably mounted to the hollow body to face inwardly in an air treatment position and to face outwardly in a surface treatment position.

In an embodiment, the apparatus comprises respective motors for each of the at least one treatment lamp to move the each between the air treatment position and to face outwardly in a surface treatment position.

In an embodiment, the apparatus comprises a controller to control a movement of the lamps and to turn on and off the at least one treatment lamp. In an embodiment, the controller comprises an interface to receive signals from at least one of an interlock sensor detecting an open and closed position of a room aperture for a room and a presence sensor detecting presence in the room, the controller configured to operate each of the at least treatment lamp in response to respective signals received. In an embodiment, the controller is configured to prevent treatment by each of the at least one treatment lamp in the surface treatment position in response to any of an interlock signal indicating an open position of the room aperture and a presence signal indicating a presence in the room.

In an embodiment, the apparatus comprises an interface to communicate with a remote control to configure operation of the controller.

In an embodiment, the controller is configured with a plurality of modes of operation comprising: an air treatment mode; a surface treatment mode; and an off mode. In an embodiment, when initiating the air treatment mode, the controller operates to: ensure the at least one treatment lamp is facing inwardly; the fan unit is on; and the at least one treatment lamp is turned on.

In an embodiment, when initiating the off mode, the controller operates to: turn off the at least one treatment lamp.

In an embodiment, when initiating the surface treatment mode, the controller operates to: ensure the at least one treatment lamp is facing outwardly; and the at least one treatment lamp is turned on; only if all doors and windows are in respective closed positions.

In an embodiment, the at least one treatment lamp comprises a plurality of treatment lamps comprising: a central treatment lamp mounted in a central position of the hollow body; and a plurality of radially spaced treatment lamps mounted about the central treatment lamp. In an embodiment, the apparatus comprises a plurality of outlets, wherein the radially spaced treatment lamps are positioned to treat air flowing therepast, when in the air treatment position, from the fan unit to the plurality of outlets.

In an embodiment, the hollow body comprises: an upper body component and a lower body component coupled in fluid communication via a central conduit, the upper body component having a surface defining the inlet and the lower body component having a surface defining the outlet. In an embodiment, the fan unit is positioned in the central conduit to drive air into the lower body component. In an embodiment, the lower body component supports an air deflector spaced from the central conduit to direct air from the fan unit to the outlet.

In an embodiment, the at least one treatment lamp comprises an UV-C lamp. The UV-C lamp is preferably an LED.

There is provided a system aspect in accordance with an embodiment where the system comprises an apparatus of any one of embodiments and a plurality of interlock sensors. The apparatus is configured to operate in the surface treatment position in response to a respective signal from the at least one interlock sensor.

In an embodiment, the system further comprises at least one presence sensor such that the apparatus is configured to operate in the surface treatment position in response to a respective signal from the at least one presence sensor. In an embodiment, the system comprises a remote control to operate the apparatus remotely.

These and other aspects will be apparent including a method aspect comprising operating an apparatus of any one of embodiments. A computer program product aspect is also provided comprising a non-transient storage device storing instructions which when executed by a processing unit configure operation of an apparatus or system herein. The operation of the apparatus and/or system also provides a computer method.

BRIEF DESCRIPTION OF THE DRAWINGS

FIG. 1 is an upper left isometric view, FIG. 2 is a side view and FIG. 3 is a lower left isometric view of an air and surface treatment device in a first or air treatment position in accordance with an embodiment.

Views herein are not necessarily to scale. Cut surfaces in cross-sectional views have hash lines omitted. Some apparatus component parts are omitted for simplicity.

Though the description herein chiefly uses the term "treat" or "treatment" in relation to the application of light to deactivate germs, a purpose of doing so is to decontaminate or sanitize the air or surfaces that are treated.

DETAILED DESCRIPTION

Figures 1, 2, 3:
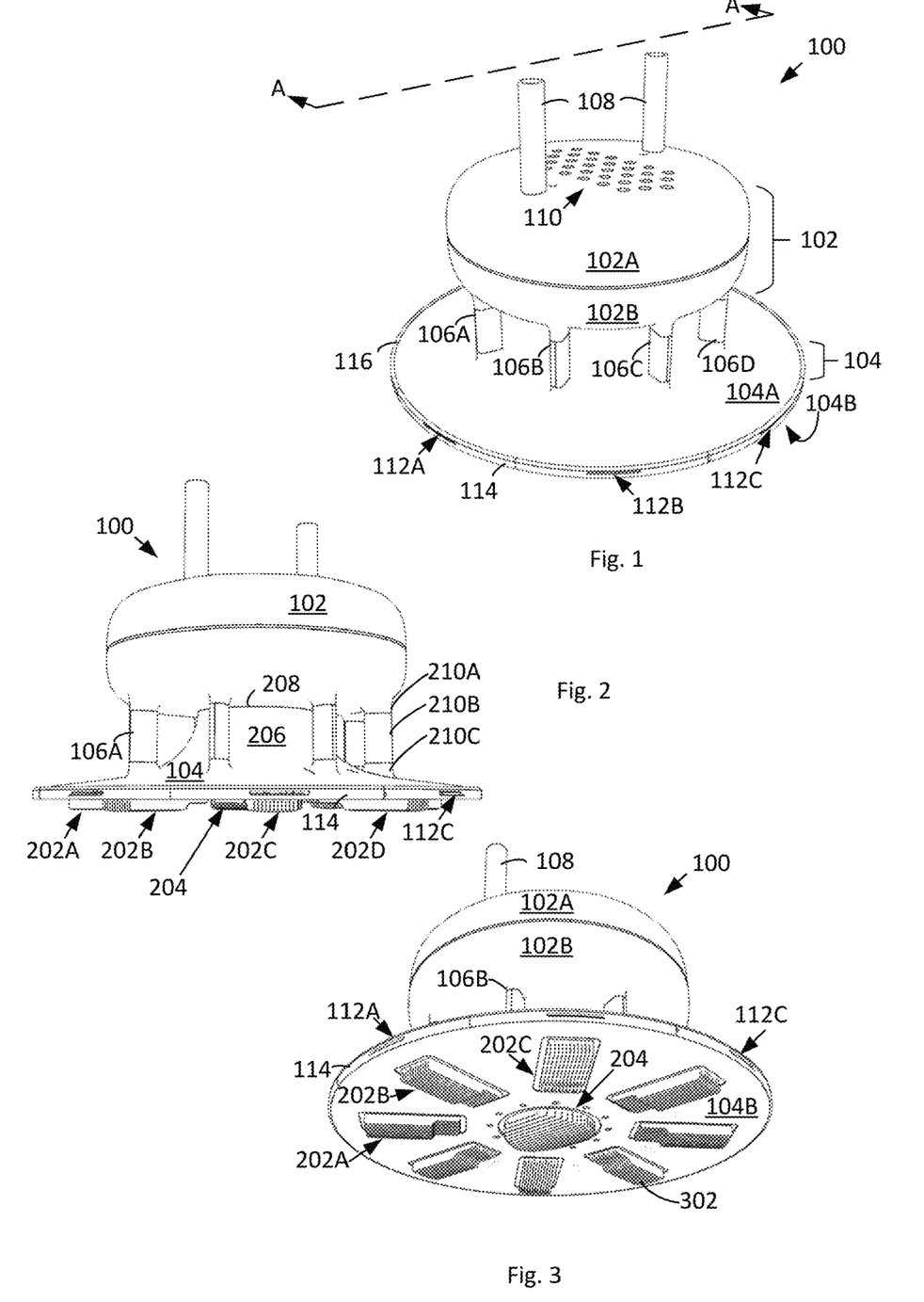

FIG. 1 is an upper left isometric view, FIG. 2 is a side view and FIG. 3 is a lower left isometric view of an air and surface treatment device 100 (an example of an apparatus and sometimes abbreviated to device 100) in a first or air treatment position in accordance with an embodiment. Device 100 comprises an upper body component 102 and a lower body component 104. Each of upper body component 102 and lower body component 104 comprise respective sub-components, for example, 102A, 102B, 104A and 104B. Upper body component 102 and a lower body component 104 are coupled together directly at a central portion of each and additionally by a plurality of spaced support columns (e.g. 106A, 106B and 106C, 106D, etc.). Posts 108, extending from upper body component 102, are useful for supporting the device 100, for example, to mount the device 100 to a ceiling (See FIG. 12).

Each of upper body component 102 and a lower body component 104 are hollow and provide for air passage therebetween. Device 100 thus comprises a hollow body chiefly defined by upper body component 102 and lower body component 104. Upper body component 102 provides (a plurality of) inlet apertures 110 in and through a surface of sub-component 102A. Lower body component 104 provides (a plurality of) outlet apertures such as 112A, 112B and 112C spaced around a peripheral surface 114.

A plurality of rectangular treatment lamps such as 202A, 202B and 202C is spaced around a central circular treatment lamp 204. In the embodiment, there is a respective rectangular treatment lamp for each respective outlet aperture. Each of the rectangular spaced treatment lamps is oriented to extend outwardly from the central lamp 204 toward the peripheral surface 114. In the embodiment, the upper and lower body components have a generally circular shape (e.g. in a horizontal cross section at their respective widest points) such that the peripheral surface 114 defines a cylinder. Peripheral surface 114 is defined by respective edges one or both of the subcomponents 104A and 104B. In the embodiment, an upper portion of the edge of subcomponent 104A defines a strengthening annular lip or rib 116.

In the embodiment, at their respective widest points, lower body component 104 is larger than upper body component 102. An upper surface 206 of lower body component 104 tapers inwardly toward the center (e.g. in a curved manner) to meet a mating central portion 208 of upper body component 102.

Figure 10:
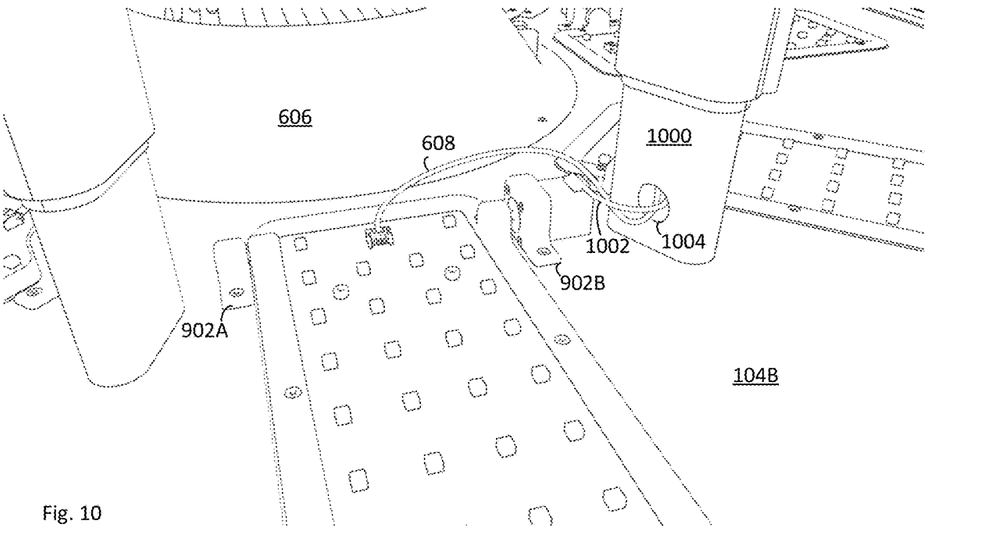
FIGS. 10 and 11 are respective enlargements of a portion of the device.

Each of the support columns (e.g. 106D) comprise an upper body projection (e.g. 210A), a central collar (e.g. 210B) and a lower body projection (e.g. 210B) surrounding a respective (inner) support tube (e.g. 1000, see FIG. 10).

The treatment lamps are shown in a first or air treatment position in FIGS. 1-3 where each of the lamps faces inwardly to treat air flowing in the hollow body between inlets and outlets. Each lamp comprise a heat sink surface (e.g. 302) such as aluminum to dissipate heat from the lamps. In the embodiment, the treatment lamps comprise LEDs to emit light in a germicidal range for treatment, such as UV-C light.

Figure 4:
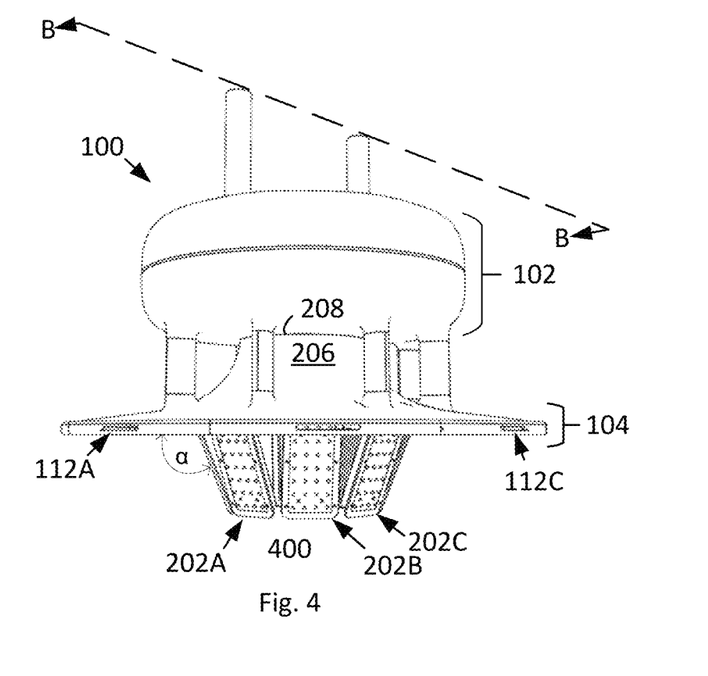
FIG. 4 is a side view and FIG. 5 is a lower left isometric view of the air and surface treatment device of FIG. 1 in a second or surface treatment position in accordance with an embodiment.
Figure 5:
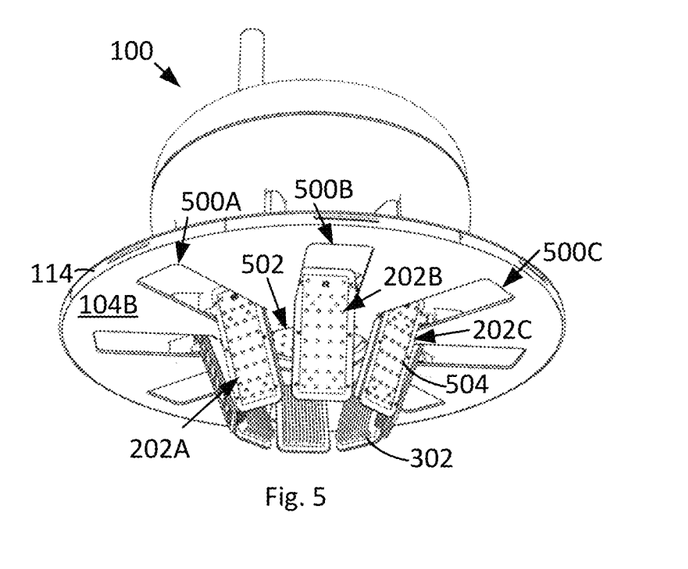

FIG. 4 is a side view and FIG. 5 is a lower left isometric view of the air and surface treatment device 100 of FIG. 1 in a second or surface treatment position in accordance with an embodiment. In FIGS. 4 and 5 the treatment lamps are shown rotated to face outwardly to treat air or external surfaces outside the device 100. Each lamp rotates through angle α, for example, 60°. Subcomponent 104B defines a plurality of respective apertures (e.g. 500A, 500B, 500C and 502) to receive respective treatment lamps (e.g. 202A, 202B, 202C and 204). Each treatment lamp comprises a plurality of LEDs (e.g. 504).

Figure 6:
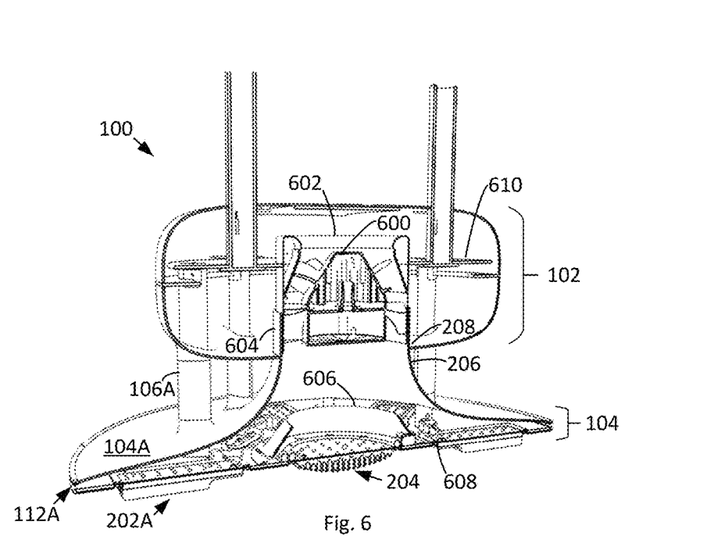
FIG. 6 is an upper left cross-sectional view of the air and surface treatment device of FIG. 1 in the first position along the line A-A of FIG. 1.
Figures 7, 8:
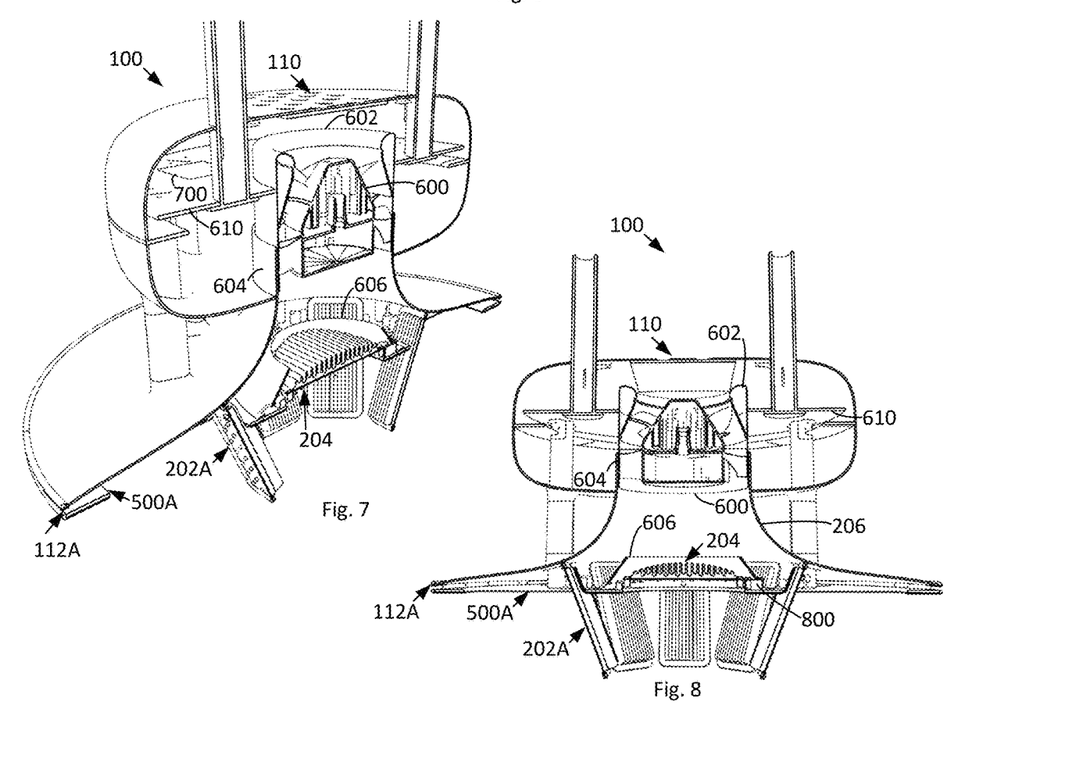
FIG. 7 is an upper left cross-sectional view and FIG. 8 is a front view of the air and surface treatment device of FIG. 4 in the second position along the line B-B of FIG. 4.

FIG. 6 is an upper left cross-sectional view of the air and surface treatment device 100 of FIG. 1 in the first position along the line A-A of FIG. 1. FIG. 7 is an upper left cross-sectional view and FIG. 8 is a front view of the air and surface treatment device 100 of FIG. 4 in the second position along the line B-B of FIG. 4. Upper body component 102 supports a fan unit 600 at mating central portion 208. Fan unit 600 is oriented to draw air through inlets 110. Though not shown, inlets 110 may be protected by a screen or similar filter (e.g. mounted adjacent the inlets on an inside of the upper body component 102) to reduce particulate matter from being drawn into the hollow body of device 100.

Fan unit 600, in the embodiment, is positioned and oriented to draw air from the upper body component 102 through a cylindrical inlet 602. An annular shaped central end portion (e.g. a cylindrical tip) 604 of upper surface 206 is received into the upper body component 102 at mating central portion 208 to interface with the fan unit 600. The central end portion 604 defines an inlet into the lower body component 104 to provide air passage in and toward the outlets (e.g. 112A, etc.)

Fan unit 600 is positioned over central treatment lamp 204. Central treatment lamp 204 is (at least partially) surrounded by an air deflector 606 to deflect air exiting from fan unit 600 toward peripheral surface 114 and the respective outlets therein (e.g. 112A, etc.) such that at least some (e.g. a majority) of the air is directed past (e.g. over) the treatment lamps 202A, etc. Some air may pass over central lamp 204. Each of the treatment lamps is wired (e.g. cable 608) as further described below. Only a portion of some of the respective cables are shown in some of the figures for clarity.

Upper body component 102 houses an interior support surface 610. The surface is mounted on ends of the support columns (e.g. 106A, etc.). Support surface is useful to mount a control component (e.g. controller board 700) and a power supply (e.g. 1100 in FIG. 11) as described further below. Support columns may be fastened (e.g. via respective collars, brackets, etc. and threaded or other fasteners, etc.) at respective ends to support surface 610 and subcomponent 104B. Subcomponents 104A and 104B may comprise in-turned peripheral edges for mating to one another. Other configurations are contemplated.

Figure 9:
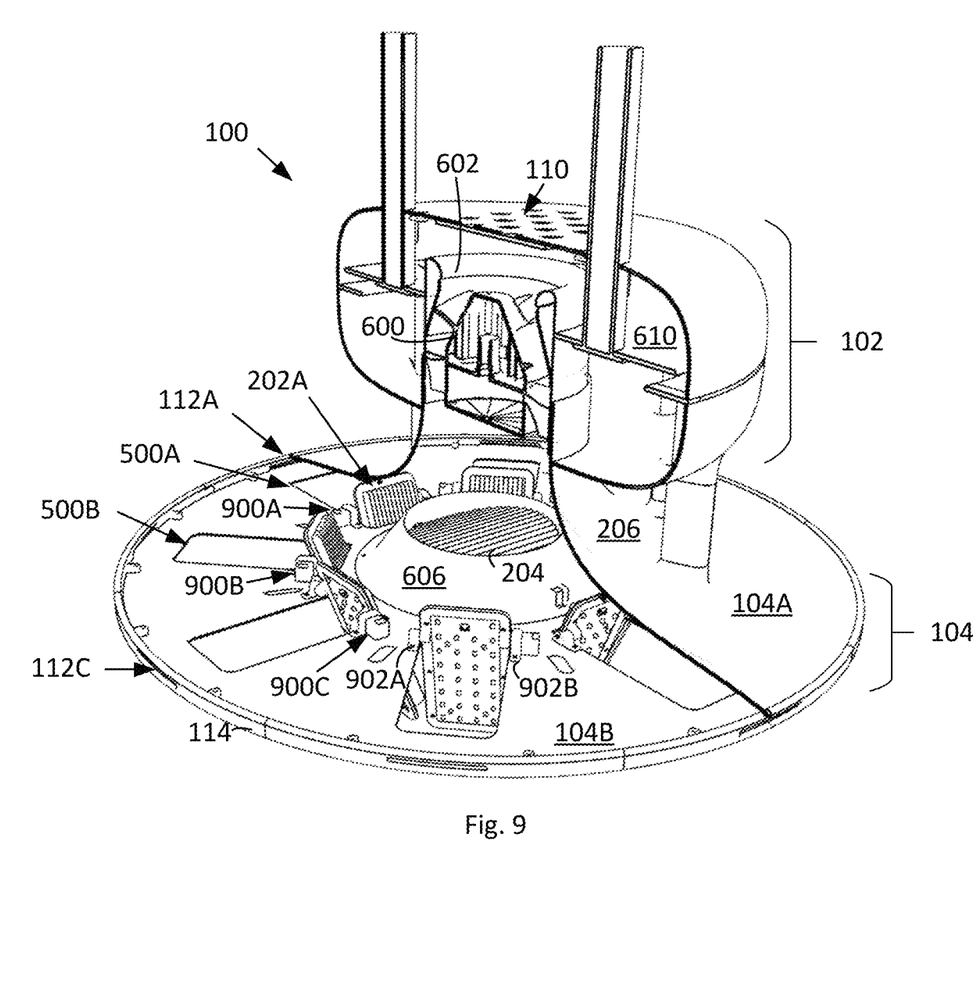
FIG. 9 is an upper right partial cross-sectional view of the air and surface treatment device of FIG. 4 in the second position along the line B-B, where a lower portion of the device is not in cross-section.
Figure 11:
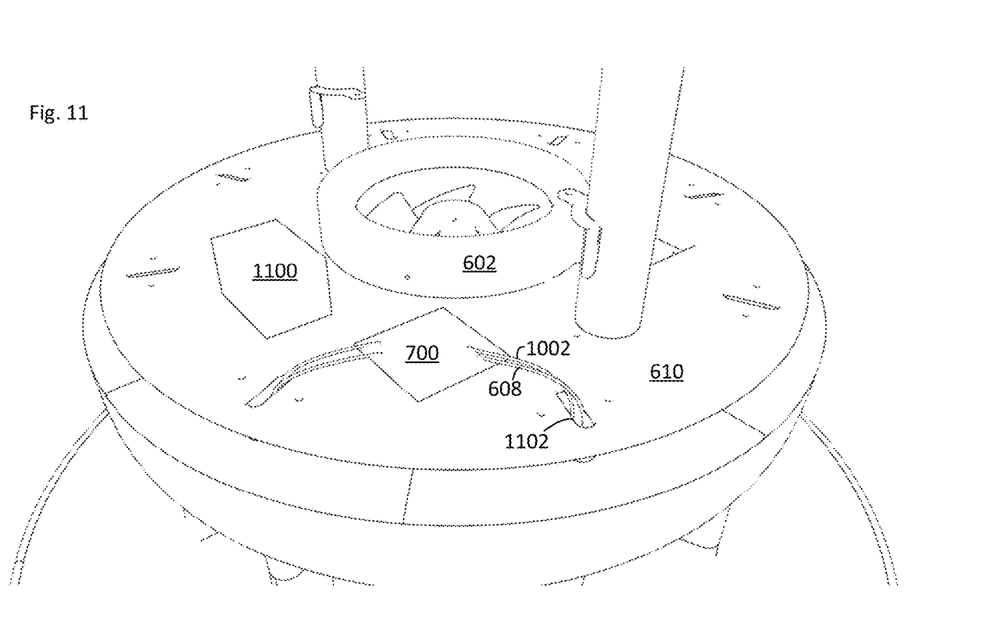
Figure 12:
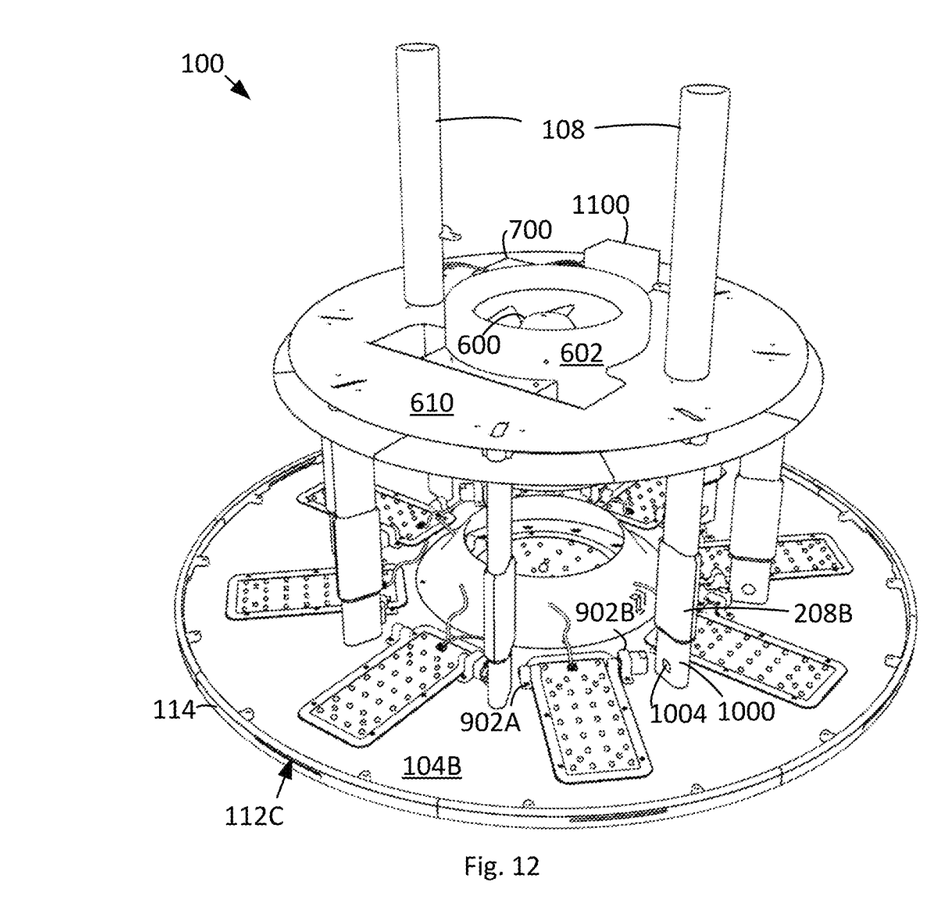
FIG. 12 is a top right isometric view of a portion of the device of FIG. 1, where outer components are removed.
Figure 13:
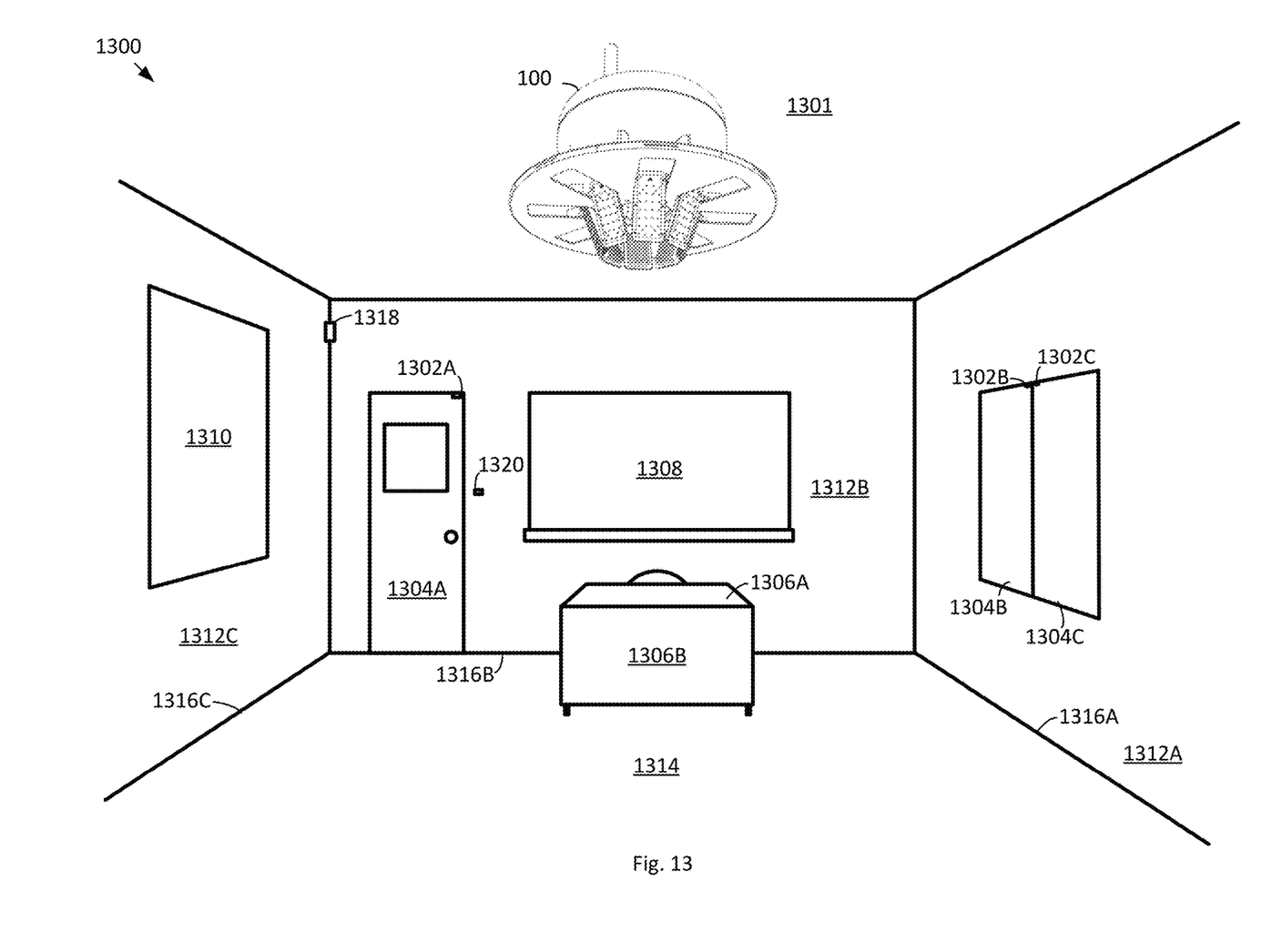
FIG. 13 is an environmental view showing the device of FIG. 5 in a classroom in accordance with an embodiment.

FIG. 9 is an upper right partial cross-sectional view of the air and surface treatment device of FIG. 4 in the second position along the line B-B, where a lower portion of the device is not in cross-section. FIGS. 10 and 11 are respective enlargements of a portion of the device 100. FIG. 12 is a top right isometric view of a portion of the device of FIG. 1, where some outer components (e.g. subcomponents 102A, 102B and 104A) are removed for clarity. Other components are removed or simplified for clarity. FIG. 13 is an environmental view showing the device of FIG. 5 in a room comprising a classroom, in accordance with an embodiment.

As noted, the treatment lamps (e.g. 202A, etc. and 204) are mounted for movement. Movement is actuated in the embodiment by respective motors (e.g. 800 for treatment lamp 204 and 900A, 900B, 900C for each of treatment lamps 202A, 202B and 202C). Cabling for the motors is not shown in at least some of the figures for clarity. In FIG. 10, lamp cabling 608 and motor cabling 1002 for one lamp and one motor associated with the one lamp is illustrated extending through aperture 1004 of support tube 1000. As shown in FIG. 11, the cabling 608, 610 extends through support tube 1000 to exit via a respective end aperture 1102 of the tube through support surface 610 in upper body component 102>the support cabling is coupled (representatively shown) to controller board 700. This illustration is simplified. Power supply 1100 is coupled to controller 700 (not shown), etc. the fan unit is powered by the supply and controlled via controller 700 e.g. via a relay (not shown) which may be mounted on surface 610.

In the embodiment, each treatment lamp comprises an axel (e.g. a pair of opposing pins, not shown) that is mounted via a pair of mounts (e.g. 902A and 902B and similarly for central lamp 204) to a surface of subcomponent 104B for rotation about the axel. One of the pins of the axel is engaged in and driven (rotated) by the respective motor for the treatment lamp. The axel from the central treatment lamp 204 is positioned about a center thereof to rotate the lamp by 180°. As noted previously, the treatment lamps that are radially spaced about the center (e.g. 202A, etc.) are mounted to rotate away from the subcomponent 104B about 60°. The respective axels are positioned toward respective ends of each treatment lamp that are adjacent the center (e.g. toward air deflector 606). In this manner the spaced treatment lamps, when rotated, face away from the center of the device 100.

In an embodiment, components of the device 100, for example 102, 104, 106A-106D, 108, among others are formed of resilient materials for the task (typically, but without limitation, one or more plastic materials and or metal materials) and are coupled via friction fit and/or fasteners (e.g. screws or other driven fasteners, etc.) using common techniques for appliance construction and assembly.

A room 1300 is shown in FIG. 13 where device 100 is mounted to a ceiling 1301 in an embodiment. Room 1300 is shown with a plurality of interlock sensors (e.g. 1302A, 1302B and 1302C and collectively 1302) for each opening aperture of the room such as door 1304A and windows 1304B and 1304C. Room 1300 comprises a plurality of surfaces such as desk surfaces 1306A, 1306B, blackboard 1308, poster board 1310, walls (e.g. 1312A, 1312B and 1312C), and floor 1314. The floor meets the respective walls at a respective junction (e.g. 1316A, 1316B and 1316C). A motion sensor 1318 (a type of presence sensor) is mounted to detect motion within the room. In an embodiment, motion sensor 1318 is integral with device 100. A motion sensor is a common type of presence sensor that senses the presence of an individual or a pet, etc. in a location. Such sensors typically use infrared detection. Other sensors that detect presence are known such as ones that detect sound, a pressure/force (e.g. walking on an area), ultrasound, environmental sensor (e.g. detecting changes in temperature, humidity, $CO_2$ due to presence of a human).

A remote control device 1320 is provided and in the embodiment is mounted to a wall within the room. In an embodiment (not shown), the remote control device 1320 is mounted outside the room (e.g. near door 1304A). The room is simplified as shown. In an embodiment, not shown, the room contains additional desks, chairs, cabinets, shelves, waste bin, etc. A classroom 1300 is a representative environment. Other environments comprise an office, a boardroom, a room in a residence (e.g. a kitchen, a living room, a bedroom, a bathroom, etc.), a hallway, etc.

As shown in FIG. 13, when mounted in a room 1300 such as on a ceiling 1301, the spaced treatment lamps, when rotated, face away from the center of the device 100. In an embodiment, the spaced treatment lamps, when rotated, face toward the junctions 1316A, 1316B and 1316C of the walls surfaces 1312A, 1312B and 1312C and a floor surface (e.g. 1314). The radial spacing of the treatment lamps directs respective lamps toward different wall surfaces spaced about the room. The central lamp 204 is directed downwardly. Any of the treatment lamps, including the central lamp, may comprise an arrangement of spaced LEDs to project a wide beam to enhance surface area coverage.

During an installation, the interlock sensors and, for example, if configured as a standalone component, the presence sensor are registered to the controller (board 700). In a configuration where the motion sensor is a component of device 100, the presence sensor typically communicates in a wired fashion and is effectively pre-registered/pre-configured with respect to the controller. An installation operation may comprise aiming the presence sensor or sensors, adjusting its (or their) field(s) of view to a desired area or areas.

Figure 14:
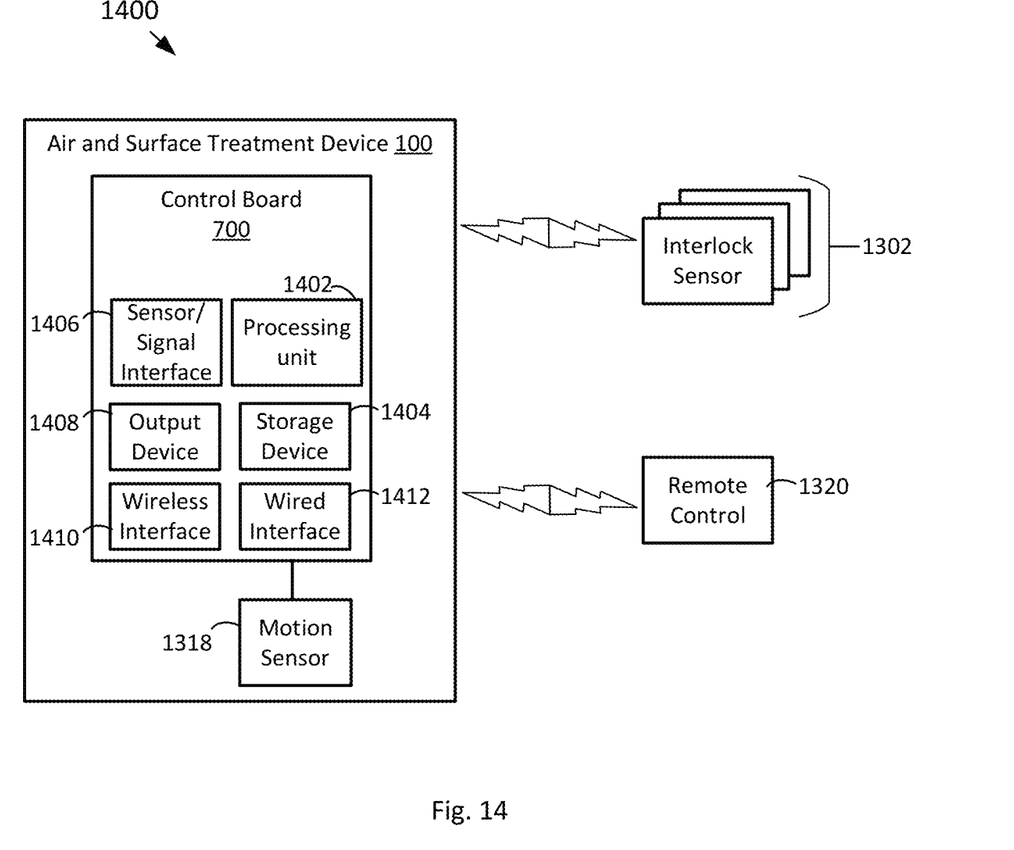
FIG. 14 is a block diagram of a system including a control board in accordance with an embodiment.

FIG. 14 is a block diagram of a system 1400 including control board 700, interlock sensors 1302, motion (presence) sensor 1318, and remote control 1320 in accordance with an embodiment. In the embodiment, control board 700 comprises a processing unit 1402, a storage unit 1404 (e.g. storing instructions, which when executed by the processing unit, configures operations of the processing unit), a signal control interface (e.g. for coupling to the treatment lamps 202A, etc., and 204, and motors (e.g. 800, 900A, etc.) and fan unit 600), an output device 1408 (e.g. one or more lights), wireless interface 1410 and a wired interface 1412

(e.g. one or more of a serial bus (e.g. USB), local area network, wide area network (e.g. telephone POTS), or other protocol/standard interface). Wireless interface 1410 comprises an antenna (not shown) and in an embodiment offers one or more wireless communication protocols (e.g. Wi-Fi and ZigBee®). In the embodiment, each of interlock sensors 1302 and remote control 1320 communicate wirelessly with the control board 700 (e.g. processing unit) according to a protocol. In this embodiment, different from the illustration of FIG. 13, the motion sensor 1318 is a component of device 100 and is coupled in a wired fashion. Components of the controller (e.g. the processing unit, etc.) may be configured as a CPU, microprocessor, microcontroller, field programmable gate array (FPGA), etc. as is known.

During an installation operation for system 1400, in accordance with the embodiment, the interlocks 1302 are registered to the controller (board 700). In accordance with the embodiment, the remote control is configured with a PIN to limit access to holders of the PIN. Mode and other setting operations are configured to require a PIN input via the remote control. In accordance with an embodiment, the remote control comprises a touch screen pad. In accordance with an embodiment, the remote control comprises output devices such as a display device, lights (for status and alarm signaling (e.g. via colors), etc.) and keys/buttons for input. In any of the remote control embodiments, the remote control comprise an audio output device such as a speaker, a bell, a chime, a buzzer, etc.

In the system 1400, in accordance with the embodiment, air and surface treatment device 100 is configured to operate in an air treatment mode, a surface treatment mode or an off mode. The surface treatment mode includes treating air in the room. The room sensors (e.g. interlock sensors 1302 and motion sensor 1318) communicate with the controller (e.g. processing unit 1402) and the controller permits or prevents operation in the surface treatment mode in response to signals received. If any interlock sensor senses an open position (of one of the room apertures) or the presence sensor senses the presence of a person (or an animal such as a pet), operation in the surface treatment mode is prevented. The lights are shut off. Optionally the lights rotate to the air treatment position.

In an example of operations, remote control 1320 communicates with the controller (e.g. control board 700) to select an operating mode. In an example, the remote control comprises an input device (not shown, e.g. a touch screen, a key pad, a button or a microphone, etc.) to receive an input to select the air treatment mode. The processing unit 1402 on board 700 receives the command (a signal from the remote control). If necessary, each of the motors 900A, etc., is commanded by the processing unit 1402 to rotate the treatment lamps (202A, etc. 204) to the air treatment position where the lamps face inwardly. The fan unit 600 is commanded to operate. The treatment lamps are turned on. The air treatment mode may remain active until commanded to stop (e.g. via remote control 1320) or until a timer duration expires. In an embodiment, a timer duration (e.g. an amount of time or time of day) may be programmable via remote control 1320. A minimum or maximum time threshold may be utilized (stored in storage device 1404 and used by processing unit) to ensure a minimum or maximum operating time.

In an example, the remote control receives an input during the air treatment mode to switch to the off mode. The processing unit 1402 on board 700 receives the command. The processing unit switches to the off mode, commanding the lamps and fan unit to turn off.

In an example, the remote control receives an input (e.g. during the air treatment mode or during the off mode) to switch to the surface treatment mode. The processing unit 1402 on board 700 receives the command. The processing unit switches to commence the surface treatment mode. In the embodiment, with the remote control on the inside of the room, prior to activating the surface treatment in the mode, the controller is configured to start a timer and a chime or other output to signal to a user to leave the room with the apertures closed within the duration of the timer. If the time expires and the interlock and presence sensors signal appropriately, the surface treatment mode is further commanded. The motors rotate the lamps to face externally. The lamps are turned on. In an embodiment, the fan unit is powered. In another, the fan unit is not powered.

The surface treatment mode may remain active until commanded to stop (e.g. via remote control 1320) or until a timer duration expires. In an embodiment, a timer duration (e.g. an amount of time or time of day) may be programmable via remote control 1320. A minimum or maximum time threshold may be utilized (stored in storage device 1404 and used by processing unit) to ensure a minimum or maximum operating time. In an embodiment, such max and min times for the surface treatment mode are independent of max and min times for the air treatment mode.

In an embodiment, the door(s) and window(s) must be closed when the initial command/input via the remote control is provided to switch to surface treatment mode. If not, the control commands an output device (e.g. on the controller or the remote control) to signal that the system is not ready. In an embodiment, the status of the interlock sensors is indicated (e.g. open or closed) such as by a light or otherwise on the remote.

During the surface treatment mode when the lamps are active (on), should a presence sensor or interlock sensor send an appropriate signal (e.g. presence detected or open aperture detected), processing unit 1402 deactivates the lamps (turns off). In an embodiment, in response, the device is switch to the off mode. A mode interrupt alarm may be sounded or displayed.

In an embodiment, controller 700 logs events such as to a portion of storage device 1404. Events comprise any of mode switches, sensor faults, other system component fault, surface treatment halted due to sensor detection, etc. Events may be associated with a respective time and date. An interface to the storage device permits access to the logged event data.

It is understood that operation of the controller (an example of a processing unit) is configurable via software (instructions) stored in a (non-transient) storage device 1404. Thus there is provided a computer program product aspect where the non-transient storage device stores instructions which when executed by a processing unit configures operation of an apparatus such as device 100 or a system herein such as the apparatus with interlock sensor(s) and optionally a presence sensor(s) and a remote control unit.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. An apparatus comprising:
   a. a hollow body comprising a first body component and a second body component coupled in fluid communication via a central conduit, the first body component having a surface defining one or more inlets and the second body component having a surface defining one or more outlets;
   b. a fan unit between the first body component and the second body component; and
   c. at least one treatment lamp to provide light to effectively inactivate germs, each at least one treatment lamp comprising an axel mounted to a distal surface of the second body component for rotation about the axel, the distal surface positioned distally relative to the upper body and wherein each at least one treatment lamp is moveably mounted about the axel to face inwardly in an air treatment position and to face outwardly in a surface treatment position and wherein at least some of the at least one treatment lamp in the surface treatment position are configured at an angle to face both of a wall surface and a floor surface for treatment.

2. The apparatus of claim 1 comprising respective motors for each of the at least one treatment lamp to move the at least one treatment lamp between the air treatment position and to face outwardly in the surface treatment position.

3. The apparatus of claim 1 comprising a controller to control a movement of the at least one treatment lamp and to turn on and off the at least one treatment lamp.

4. The apparatus of claim 3, wherein the controller comprises an interface to receive signals from at least one interlock sensor detecting an open and closed position of an at least one room aperture for a room and an at least one presence sensor detecting presence in the room, the controller configured to operate each of the at least treatment lamp in response to respective signals received.

5. The apparatus of claim 3, wherein the controller is configured to prevent treatment by each of the at least one treatment lamp in the surface treatment position in response to any of an interlock signal indicating an open position of the at least one room aperture and a presence signal indicating a presence in the room.

6. The apparatus of claim 3 comprising an interface to communicate with a remote control to configure operation of the controller.

7. The apparatus of claim 3, wherein the controller is configured with a plurality of modes of operation comprising:
   a. an air treatment mode;
   b. a surface treatment mode; and
   c. an off mode.

8. The apparatus of claim 7, wherein when initiating the air treatment mode, the controller operates to:
   a. ensure the at least one treatment lamp is facing inwardly;
   b. the fan unit is on; and
   c. the at least one treatment lamp is turned on.

9. The apparatus of claim 7, wherein when initiating the off mode, the controller operates to:
   a. turn off the at least one treatment lamp.

10. The apparatus of claim 7, wherein when initiating the surface treatment mode, the controller operates to:
    a. ensure the at least one treatment lamp is facing outwardly; and
    b. the at least one treatment lamp is turned on;
    only if each of the at least one room aperture is in a respective closed position.

11. The apparatus of claim 1, wherein the at least one treatment lamp comprises a plurality of treatment lamps comprising:
    a. a central treatment lamp mounted in a central position of the hollow body; and
    b. a plurality of radially spaced treatment lamps mounted to ring around the central treatment lamp in the air treatment position and the surface treatment position.

12. The apparatus of claim 11 comprising a plurality of outlets, wherein each of the radially spaced treatment lamps extends away from the central treatment lamp toward one of the plurality of outlets to treat air flowing therepast, when in the air treatment position, from the fan unit to the plurality of outlets.

13. The apparatus of claim 1, wherein the fan unit is positioned in the central conduit to drive air into the second body component to exit radially outward from the second body component.

14. The apparatus of claim 13, wherein the second body component supports an air deflector spaced from the central conduit to direct air from the fan unit to the plurality of outlets.

15. The apparatus of claim 1, wherein the at least one treatment lamp comprises an UV-C lamp.

16. A system comprising:
    an apparatus comprising:
    a. a hollow body comprising a first body component and a second body component coupled in fluid communication via a central conduit, the first body component having a surface defining one or more inlets and the second body component having a surface defining one or more outlets;
    b. a fan unit between the first body component and the second body component; and
    c. at least one treatment lamp to provide light to effectively inactivate germs, each at least one treatment lamp comprising an axel mounted to a distal surface of the second body component for rotation about the axel, the distal surface positioned distally relative to the upper body, and wherein each at least one treatment lamp is moveably mounted about the axel to face inwardly in an air treatment position and to face outwardly in a surface treatment position and wherein at least some of the at least one treatment lamp in the surface treatment position are configured at an angle to face both of a wall surface and a floor surface for treatment; and d. a controller to control operation of the apparatus; and at least one interlock sensor;

wherein the controller is configured to operate the apparatus in the surface treatment position in response to a respective signal from the at least one interlock sensor.

17. A system comprising:

an apparatus comprising:
- a. a hollow body having an inlet and an outlet;
- b. a fan unit between the inlet and the outlet; and
- c. at least one treatment lamp to provide light to effectively inactivate germs, each at least one treatment lamp moveably mounted to the hollow body to face inwardly in an air treatment position and to face outwardly in a surface treatment position; and
- d. a controller to control operation of the apparatus; and at least one interlock sensor;

at least one presence sensor; and wherein the controller is configured to operate the apparatus in the surface treatment position in response to respective signals from the at least one interlock sensor and the at least one presence sensor.

18. The system of claim 16 comprising a remote control to operate the apparatus remotely via the controller.

19. The system of claim 16, wherein the controller is configured with a plurality of modes of operation comprising:
- a. an air treatment mode;
- b. a surface treatment mode; and
- c. an off mode.

20. The apparatus of claim 11, wherein the central treatment lamp is at least partially surrounded by the air deflector to deflect a majority of the air exiting from the fan unit toward the plurality of outlets and past the radially spaced treatment lamps when in an air treatment position.

* * * * *